United States Patent [19]
Gompper et al.

[11] Patent Number: 5,646,295
[45] Date of Patent: Jul. 8, 1997

[54] DIAZAPENTALENE DERIVATIVES AS A SPECIFIC REAGENT FOR THIOL COMPOUNDS

[75] Inventors: Rudolf Gompper, München; Manfred Kubbies, Penzberg; Axel Schmidt, München; Bernhard Virnekas, München, all of Germany

[73] Assignee: Boehringer Mannheim GmbH, Mannheim, Germany

[21] Appl. No.: 586,826

[22] PCT Filed: May 25, 1995

[86] PCT No.: PCT/EP95/01981

§ 371 Date: Jan. 31, 1996

§ 102(e) Date: Jan. 31, 1996

[87] PCT Pub. No.: WO95/32969

PCT Pub. Date: Dec. 7, 1995

[30] Foreign Application Priority Data

Jun. 1, 1994 [DE] Germany ............... 44 19 097.2

[51] Int. Cl.$^6$ ................. C07D 403/04; C07D 487/02; C07D 209/52; C07F 9/02; G01N 33/48; G01N 33/00

[52] U.S. Cl. ............... 548/311.7; 435/40.5; 436/63; 436/120; 548/305.1; 548/312.1; 548/364.7; 548/412; 548/444; 548/452; 548/453; 548/262.4; 548/252; 548/253; 548/255; 548/260; 548/261; 548/266.4; 548/362.5; 548/119; 548/302.7; 548/469; 548/969; 546/256; 546/277.4; 544/333; 544/242; 544/294; 558/307

[58] Field of Search ................. 548/311.7, 412, 548/312.1, 364.7, 255, 362.5, 266.4, 260, 261, 305.1, 252, 253, 453, 262.4, 444, 452; 546/271; 544/333; 435/40.5, 63, 120; 436/63, 120

[56] References Cited

U.S. PATENT DOCUMENTS 4,914,211  4/1990  Jost et al. ............... 548/453

OTHER PUBLICATIONS

"(Hetero)Pentalene Derivatives and Y–Shaped Carbodications", F. Closs et al, *Synthetic Metals*, 29(1989) E537–E544.

"Chemistry of Organic Compounds", 3rd Ed., Carl R. Noller (1965), p. 119.

*Primary Examiner*—Johann Richter
*Assistant Examiner*—Jane C. Osweckí
*Attorney, Agent, or Firm*—Nikaido Marmelstein Murray & Oram LLP

[57] ABSTRACT

The invention concerns diazapentalene derivatives of formula I

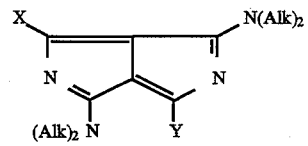

in which X and Y represent leaving groups which are less nucleophilic than thiol compounds, as thiol-specific fluorochromes for the detection of compounds containing thiol groups, in particular in cells.

19 Claims, No Drawings

DIAZAPENTALENE DERIVATIVES AS A SPECIFIC REAGENT FOR THIOL COMPOUNDS

This application is a 371 of PCT/EP95/01981 May 25, 1995.

The invention concerns diazapentalene derivatives and their use as a fluorochrome specific for thiol groups in particular for cell staining as well as a method for the fluorimetric detection of compounds containing thiol groups especially in cells.

Of numerous known fluorescent compounds that react with thiol groups only a few fulfil the condition that this reaction should be sufficiently selective.

An important area of application of fluorochromes that react selectively with thiol groups is in general the analysis of compounds which contain thiol groups (in particular proteins), for example the detection of such compounds in HPLC analysis, in thin layer chromatography or in gel electrophoresis.

A special area of application of such specific reagents for thiol groups is the staining of living cells. In this case the fluorochrome reagents that are specific for thiol groups must be able to penetrate into the cell in order to be able to react with the thiols present there and in particular with glutathione and cysteine residues. The content and under some circumstances also the position of thiols and in particular of glutathione in the cell can be determined by measuring the fluorescence of the cells stained in this manner. Since one of the functions of glutathione in the cell is to render mutagens or carcinogens harmless, the determination of the cellular content of glutathione also provides information on the protection of the cell against harmful influences. Furthermore cellular thiols, in particular glutathione, are involved in a number of other biochemical processes so that their cellular content can be associated with a number of pathological diseases (see for example J. Bio. Chem. 263, 17205).

After the cells have been incubated with a thiol-specific fluorochrome, the content of fluorescent thiol adducts in the cell is preferably determined by means of flow cytometry or by digital video imaging. Flow cytometry has the very advantageous property of being able to measure physiological parameters in a large number of living single cells. It even allows the determination of heterogeneities within a cell population. In this method the fluorescence of individual cells in a liquid current is determined by means of fluorescent optics preferably after excitation with an argon laser at 488 nm (Flow Cytometry and Sorting, M. R. Melamed et al. (eds) Wiley and Liss, 1990). A review of the determination of thiols in cells by flow cytometry is given by Rabinowitch et al. in Clinical Flow Cytometry, K. D. Bauer et al. (eds) Williams and Wilkins, 1993, page 505–534, Durant et al., Radiation Research 95, 456–470 (1983) and McLean Grogan, Guide to Flow Cytometry Methods, Marcel Dekker Inc., New York and Basel, (1990), page 171–176. These literature references also give a review of conventional fluorochrome reagents that are specific for thiol groups for flow cytometry. Maleimide derivatives and bromobimane are described in these references as being the most common.

Disadvantages of the fluorochrome thiol-specific reagents for cell staining described in the state of the art are that some of them have a high cell toxicity (bromobimane), can only penetrate into the cells with difficulty (fluorescein-5-maleimide, didansyl cystine), have an unfavourable excitation wavelength for the excitation wavelength especially of common argon lasers (bimane at 360–400 nm, 3-4-maleimidylphenyl-4-methyl-7-diethylamino-coumarin (CPM): at 395 nm, didansyl cystine: 335 nm), have slow addition kinetics (chlorobimane, CPM) and must therefore be used in high concentrations or they have an inadequate specificity for thiol groups (orthophthaldialdehyde). In addition most of the known compounds have a low photostability which is a disadvantage particularly when observing the cells over a long time period under a microscope e.g. under a mercury vapour lamp.

The object of the present invention was therefore to eliminate the disadvantages of the thiol-specific fluorochrome compounds of the state of the art and to provide fluorochrome reagents which react very specifically and rapidly with thiol groups, which penetrate rapidly into cells and have a low cell toxicity, which can be used at a favourable excitation wavelength for an argon laser, which have a high photostability and can therefore be used advantageously for cell staining and especially in flow cytometry.

The object is achieved by the invention as characterized in the claims.

The invention concerns diazapentalene derivatives of formula I

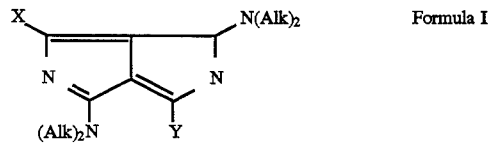

Formula I in which X and Y are the same or different and represent a leaving group which is less nucleophilic than a thiol compound.

Such leaving groups are known to a person skilled in the art. Preferred examples are heterocycles containing nitrogen such as pyrazoles, benzopyrazoles, imidazoles, benzimidazoles, triazoles and benztriazoles, tetrazoles, pyrrole, indole, carbazole and pyrimidine groups, aromatic leaving groups such as hydroxy-, alkoxy-, carboxy-, alkoxycarbonyl-, nitro-, amino-, alkylamino-, dialkylamino-substituted phenyl or pyridine, triphenyl-phosphonium, tosyl and halides and pseudohalides such as fluorine, chlorine, bromine, iodine, SCN, $N_3$ etc.

The imidazole group is particularly preferred as the leaving group.

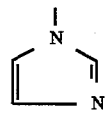

The alkyl groups at the amino nitrogen preferably have 1–6 C atoms, the methyl group being particularly preferred.

The aromatic or heteroaromatic leaving groups can of course also be substituted in particular by such groups which render the leaving groups less nucleophilic. In the case of nitrogen-containing heteroaromatics, nitrogen atoms can for example be substituted, in particular alkylated. As long as these substituents do not render the leaving group more nucleophilic than a thiol group, the type of substituent is not important for the invention.

An alkyl group is particularly preferably understood as a $C_1$-$C_6$ alkyl group.

The invention also concerns a method for the specific detection of compounds containing thiol groups in a sample by reacting the sample with a fluorochrome that reacts with thiol groups and measuring the fluorescence of the reaction products as a measure for the presence or amount of thiol compound in the sample characterized in that the fluorochrome reacting with a thiol group is a diazapentalene derivative according to formula I.

The method is carried out such that the fluorochromes according to the invention are incubated preferably in an excess with the thiol compounds to be detected in solution, preferably in an aqueous solution, and the fluorescent products that are formed are measured. The excitation wavelength in the measurement is preferably between 460 and 500 nm, the measuring wavelength is preferably above 510 nm.

The compounds to be detected can contain free thiol groups as such or thiol groups can be introduced chemically into the compounds by known methods in order to then be able to detect them with the fluorochromes according to the invention.

Thus the fluorochromes according to the invention are also very suitable as fluorescent marker molecules for molecules containing thiol groups or for molecules which have been modified with thiol groups (e.g. thiol-modified nucleotides, proteins, thiol-modified lipids) and in particular as fluorescent conjugates of haptens, antigens or antibodies for immunoassays.

The detection method according to the invention for compounds containing thiol groups can be used advantageously for the qualitative or quantitative detection of one or several substances containing thiol groups in a chromatographic separation e.g. a HPLC separation or a gel electrophoresis by reacting the sample with the fluorochromes according to the invention before the separation and detecting the compounds containing thiol groups, such as proteins, fluorometrically during the chromatographic separation. In contrast in the case of a separation by thin-layer chromatography, the separated thiol compounds can be preferably rendered detectable by spraying the fluorochromes according to the invention onto the thin-layer plate.

The invention additionally concerns a method for the specific determination of components of a cell containing thiol groups by incubating the cells with a fluorochrome that reacts with thiol groups and measuring the fluorescence of the reaction products as a measure for the presence or amount of thiol groups in the cell characterized in that the fluorochrome reacting with a thiol group is a compound according to formula I.

The method is carried out such that cells are incubated with the fluorochrome according to the invention preferably in an aqueous solution.

The cell concentration in this method is usually between $10^4$ and $10^8$ cells per ml, preferably between $10^5$ and $10^7$ cells per ml.

The concentration of the fluorochrome according to the invention is between 10 ng/ml and 10 µg/ml, preferably between 50 ng and 500 ng/ml and quite especially preferably 70–200 ng/ml depending on the cell type, cell size and the cell-physiological state. These are lower concentrations than those required by the state of the art to stain the cell.

The incubation period is generally between 5 and 30 minutes. Even after 10 minutes it is possible to achieve an almost complete reaction.

The fluorescence can be measured by various methods e.g. fluorescence microscopy. In this case the cells are labelled with the fluorochrome according to the invention under the aforementioned preferred conditions, mounted on a slide and covered with a cover slip. Subsequently the labelled cells are observed through a conventional fluorescence microscope, the excitation wavelength being preferably between 460 and 500 nm. High pressure mercury lamps and xenon lamps come into consideration for the fluorochrome excitation. The optical colour dividers and emission filters are preferably selected such that the emitted fluorescence is available above a wavelength of 510 nm for visual observation or camera recording for quantitative digital image cytometry.

In a special method the cells can also be analysed by means of confocal high resolution microscopy and the fluorescence can be quantified. Depending on the confocal measuring technique, either the aforementioned light sources again come into consideration as excitation light sources or lasers with emission wavelengths in the aforementioned range.

Measurement by means of flow cytometry is particularly preferred in which individual cells are analysed with regard to their fluorescent properties at a high flow rate.

The excitation wavelength in all fluorescent measurements is preferably between 460 and 500 nm which is the excitation wavelength of the argon laser. The measuring wavelength is preferably above 510 nm.

The fluorochromes according to the invention stain the cells with a high thiol specificity. They only have a low cytotoxicity (>100 ng/ml) and exhibit rapid saturation kinetics i.e. saturation is already achieved after 10 min (80–90 % of the maximum fluorescence) using only 100 ng/ml fluorochrome incubated with only $10^6$ cells. Moreover the fluorochrome-labelled cells have a high photostability.

The invention in addition concerns the use of the thiol-specific fluorochromes according to the invention for the determination of compounds containing thiol groups.

The invention in addition concerns the use of the fluorochromes according to the invention for flow cytometry and cell diagnostics.

Furthermore the invention concerns a process for the production of the fluorochromes according to the invention.

The fluorochromes according to the invention are synthesized by reacting one equivalent of dichlorodiazapentalene with two equivalents of a nucleophile X' and/or Y' which is more nucleophilic than chlorine but less nucleophilic than a thiol compound. The preparation of the starting compound dichlorodiazapentalene is described in F. Closs et al., "Angew. Chem." 100, 875 (1988).

In this process reaction of the fluorochromes according to the invention with thiol groups is carried out such that in the main only one leaving group X or Y is substituted by a residue R—SH bound to a thiol group. The thioether compounds III are mainly obtained in this process which have a strong fluorescence with a high quantum yield. If the reaction period is longer and in particular if the temperature is higher than room temperature, both leaving groups X and Y may also be substituted by a residue bound to a thiol group.

The invention additionally concerns the resulting fluorescent compounds of formula III and IV,

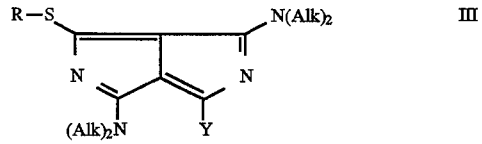

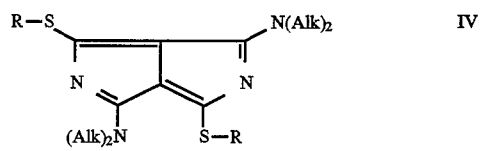

in which Y is defined as above and R is a residue bound to a thiol group of a molecule to be detected such as for example a protein, a (modified) nucleotide, a (modified) lipid, glutathione, a hapten, an antibody or an antigen.

The invention in addition concerns the use of the fluorochromes according to the invention as markers for compounds containing thiol groups and the use of compounds according to formula III or IV as fluorescent conjugates for example in immunoassays.

EXAMPLE 1

Example of application in flow cytometry: Jurkat T cells are resuspended in PBS at a concentration of $10^6$ cells per ml and admixed with 100 ng/ml of the fluorochrome diimidazolodiazapentalene. The cells are incubated for 10 minutes at 37° C. Since the fluorochromes that do not react with SH groups do not fluoresce, no washing i.e. removal of unbound fluorochromes is necessary. The labelled Jurkat cells are analysed in a flow cytometer (e.g. Cytofluorograph, Ortho Instruments or FACSstar plus, Becton Dickinson) in which the fluorochrome is excited by an argon laser at 488 nm and 50 mW and the cell flow rate is 600 cells per second. The emitted fluorescence is measured through a long pass emission filter which has a pass band larger than 510 nm. The intensity distribution of the cells is represented by a one-dimensional fluorescence histogram.

In order to exclude unspecific labelling of the cells, a living/dead counter-staining with propidium iodide is carried out in which ca. 1 μg/ml of this fluorochrome is added either already during the incubation with the fluorochrome according to the invention or shortly before the measurement. The data are then analysed by a two-dimensional cytogram.

Furthermore further fluorescent cell labels can also be used together with the fluorochromes according to the invention in which case the emission wavelength of the other fluorochromes should preferably be above 580 nm. In particular cell labelling with monoclonal antibodies which are in turn fluorescent labelled can be used (e.g. phycoerythrin).

EXAMPLE 2

Synthesis of 1,4-bis(dimethylamino)-3,6-diimidazole-1-pyrrolo(3,4-c)pyrrole 4.00 g (15.4 mmol) 1,4-bis(dimethylamino)-3,6-dichloro-1-pyrrolo(3,4-c)pyrrole was admixed with 6.81 g (100 mmol) imidazole in 100 ml acetonitrile and the mixture was stirred for 2 hours at 60° C. After cooling to 0° C., the precipitate was suction filtered and washed with acetonitrile and ether. Yield: 4.77 g (96 %) red, green shiny crystals (from acetonitrile), melting point 259° C. (decomp.).

IR (Nujol): v=3100 cm$^{-1}$, 1599, 1540, 1408, 1331, 1312, 1279, 1050, 988, 918. —UV/Vis (CH$_3$CN): max (1 g)=275 nm (4.114), 304 (sh), 470 (sh), 501 (4.445). —UV/Vis (CH$_3$COOH): max(qual.)=218 nm, 268, 310 (sh), 476 (sh), 507–1H-NMR (CDCl$_3$): δ=3.05 (s, 12 H, NCH$_3$), 7.13 (dd, 2H, 4'-H or 5'-H), 7.36 (dd, 2H, 4'H or 5'H), 7.91 (dd, 2H, 2'H)-13C-NMR (CDC$_3$): δ=40.69 (q, NCH$_3$), 109.99 (s, C-3a, C-6a), 120.27 (d, C-5'), 129.47 (d, C-4'), 138.09 (d, C-2'), 149.73 (s, C-3, C-6), 158.55 (s, C-1, C-4). MS (70 eV), m/z (%) [M*], 307 (8) [M*-CH$_3$], 322 (100) [M*].

We claim:

1. A diazapentalene compound suitable for use as a thiol group-specific fluorochrome, said compound of the formula

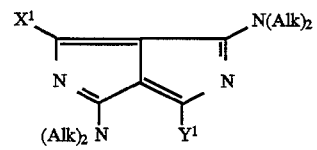

wherein

Alk is $C_1$-$C_6$ alkyl, and $X^1$ and $Y^1$ are independently each a leaving group that is less nucleophilic than a thiol compound, which leaving group is other than chlorine.

2. The compound of claim 1, wherein the leaving groups are independently a pyrazole, benzopyrazole, imidazole, benzimidazole, triazole, benzotriazole, tetrazole, pyrrole, indole, carbazole or pyrimidine group, triphenylphosphonium, tosyl, fluorine, bromine, iodine, SCN, azide, or a phenyl or pyridine group substituted with hydroxy, alkoxy, alkoxycarbonyl, carboxy, amino, monoalkylamino, dialkylamino or nitro.

3. The compound of claim 1, wherein at least one leaving group is an imidazole group.

4. The compound of claim 3, wherein both leaving groups are imidazole groups.

5. A method for the specific detection of compounds containing thiol groups in a sample, comprising reacting the sample with a fluorochrome of the formula

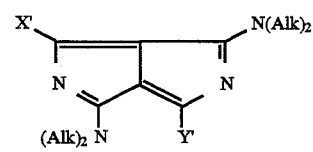

wherein Akl is $C_1$-$C_6$ alkyl, and $X^1$ and $Y^1$ are independently each a leaving group that is less nucleophilic than a thiol compound, to obtain a reaction product, and measuring the fluorescence of the reaction product to determine the presence or the amount of thiol compounds in the sample.

6. The method of claim 5, wherein the leaving groups are independently selected from the group consisting of a pyrazole, benzopyrazole, imidazole, benzimidazole, triazole, benzotriazole, tetrazole, pyrrole, indole, carbazole or pyrimidine group, triphenylphosphonium, tosyl, fluorine, chlorine, bromine, iodine, SCN, azide or a phenyl or pyridine group substituted with hydroxy, alkoxy, alkoxycarbonyl, carboxy, amino, alkylamine, dialkylamino or nitro.

7. The method of claim 6, wherein at least one leaving group is an imidazole groups.

8. The method of claim 7, wherein both leaving groups are imidazole groups.

9. The methods of claim 5, wherein the reaction product is excited at a wavelength of between 460 and 500 nm, and the fluorescence is measured at a wavelength above 510 nm.

10. The methods of claim 5, wherein thiol group-containing compounds are detected during or after a chromatographic separation.

11. The method of claim 5, wherein the sample is a cell sample.

12. The method of claim 11, wherein the fluorochrome is used at a concentration of 10 ng/ml to 10 μg/ml.

13. The method of claim 11, wherein the detection of the fluorescence is by fluorescence microscopy.

14. The method of claim 11, wherein the detection of the fluorescence is by digital video imaging.

15. The method of claim 11, wherein the detection of the fluorescence is by confocal microscopy.

16. The method of claim 11, wherein glutathione is determined.

17. A method of marking a compound containing thiol groups, said method comprising reacting the compound with a fluorochrome of the formula

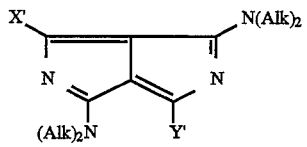

I wherein Alk is $C_1$-$C_6$ alkyl, and $X^1$ and $Y^1$ are independently each a leaving group that is less nucleophilic than a thiol compound.

18. A process for producing the compounds of claim 1, comprising reacting one equivalent of dichlorodiazapentalene of the formula

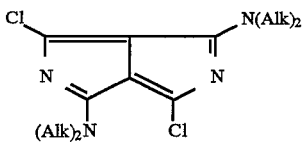

II wherein Alk is $C_1$-$C_6$ alkyl, with two equivalents of a nucleophile $X^1$ and/or $Y^1$ which is more nucleophilic than chloride but less nucleophilic than a thiol compound.

19. Method of claim 11, wherein the detection of the fluorescence is by flow cytometry.

* * * * *